United States Patent
Mitani

(10) Patent No.: US 10,429,227 B2
(45) Date of Patent: Oct. 1, 2019

(54) ELECTRIC WAVE TYPE BIOSENSOR

(71) Applicant: Shigetomo Mitani, Aichi (JP)

(72) Inventor: Shigetomo Mitani, Aichi (JP)

(73) Assignee: OMRON CORPORATION, Kyoto (JP)

( * ) Notice: Subject to any disclaimer, the term of this patent is extended or adjusted under 35 U.S.C. 154(b) by 81 days.

(21) Appl. No.: 15/628,530

(22) Filed: Jun. 20, 2017

(65) Prior Publication Data

US 2017/0363458 A1  Dec. 21, 2017

(30) Foreign Application Priority Data

Jun. 21, 2016  (JP) .................................. 2016-122689

(51) Int. Cl.
| | |
|---|---|
| *G01F 23/26* | (2006.01) |
| *G01N 27/22* | (2006.01) |
| *G01N 27/416* | (2006.01) |
| *A61B 5/05* | (2006.01) |
| *G01N 27/00* | (2006.01) |

(52) U.S. Cl.
CPC ............ *G01F 23/26* (2013.01); *A61B 5/0507* (2013.01); *G01N 27/22* (2013.01); *G01N 27/416* (2013.01); *G01N 27/00* (2013.01)

(58) Field of Classification Search
None
See application file for complete search history.

(56) References Cited

U.S. PATENT DOCUMENTS

| | | | |
|---|---|---|---|
| 2017/0016221 A1 | 1/2017 | Yamamoto et al. | |
| 2018/0120420 A1* | 5/2018 | McMahon | G01S 13/56 |
| 2018/0170213 A1* | 6/2018 | Lu-Dac | A61B 5/0507 |

FOREIGN PATENT DOCUMENTS

| | | |
|---|---|---|
| CN | 103340619 A | 10/2013 |
| JP | 2006055504 A | 3/2006 |
| JP | 2010120493 A | 6/2010 |
| JP | 2011015887 A | 1/2011 |
| JP | 2014-126523 A | 7/2014 |
| WO | 2015-087541 A1 | 6/2015 |
| WO | 2015-140333 A1 | 9/2015 |

OTHER PUBLICATIONS

Notice of Reasons for Refusal issued in Japanese Application No. 2016-122689, dated Jun. 4, 2019 (6 pages).

* cited by examiner

*Primary Examiner* — Douglas X Rodriguez
(74) *Attorney, Agent, or Firm* — Osha Liang LLP

(57) ABSTRACT

An electric wave type biosensor includes: an electromagnetic wave irradiation unit; and a reflected wave receiving unit which receives a reflected wave and obtains an I signal obtained by multiplying the irradiated electromagnetic wave signal and the received reflected signal, and a Q signal obtained by delaying the I signal only by a predetermined phase. The electric wave type biosensor further includes: a differentiation calculation unit which differentiates the I signal and the Q signal and calculates an I signal differential value and a Q signal differential value; and an angular velocity calculation unit which calculates an angular velocity of the I signal and the Q signal, based on the I signal and the Q signal and the I signal differential value and the Q signal differential value.

3 Claims, 7 Drawing Sheets

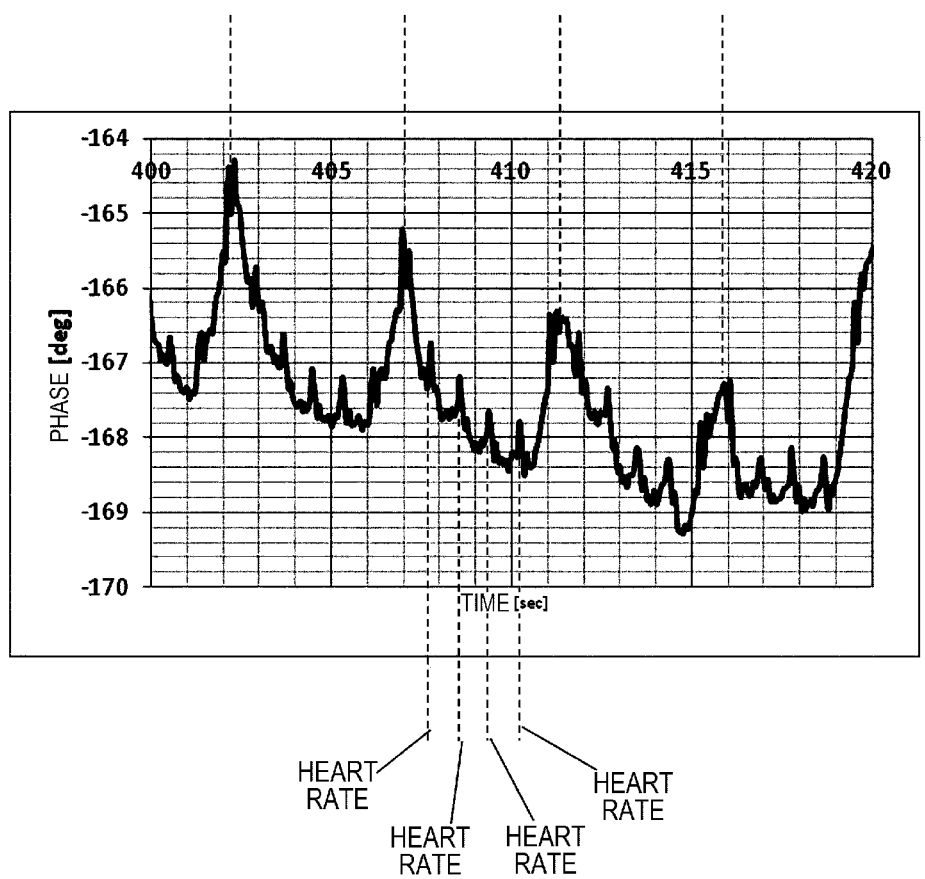

ELECTRIC WAVE TYPE BIOSENSOR

CROSS-REFERENCES TO RELATED APPLICATIONS

This application is based upon and claims the benefit of priority from Japanese Patent Application No. 2016-122689, filed on Jun. 21, 2016, the entire contents of which are incorporated herein by reference.

FIELD

One or more embodiments of the present invention relate to an electric wave type biosensor that uses a Doppler sensor.

BACKGROUND

From the related art, a technology which irradiates a human body surface with an electromagnetic wave by using a Doppler sensor and obtains bio-information included in a reflected wave based on a coordinate plane configured of an I signal and a Q signal of the reflected wave, is known. For example, JP-A-2006-055504 discloses a heart rate measuring apparatus which detects an output signal including an amplitude component and a phase component of a reflected wave from a human body surface by using an electric wave type Doppler sensor, and extracts only a heart rate component by separating the amplitude component generated by body movement of a human body. The heart rate measuring apparatus outputs an amplitude component signal and a phase component signal to a heart rate extractor by performing polar coordinate conversion using an amplitude and phase converter with respect to an output signal (an I signal and a Q signal) including information of the amplitude component and the phase component of the reflected wave output by the electric wave Doppler sensor. The heart rate extractor extracts only accurate heart rate by separating the amplitude component generated by the body movement included in the amplitude component output from the amplitude component signal and the phase component signal by using a method of independent component analysis.

In addition, JP-A-2010-120493 discloses a bio-signal sensing apparatus which prevents deterioration of accuracy of a bio-signal of an occupant. The bio-signal sensing apparatus includes: a sensor unit which senses movement of the occupant by an electric wave type non-modulation Doppler sensor; a bio-signal extract unit which extracts a bio-signal of the occupant based on a phase change of an output of the sensor unit; a distance calculation unit which calculates an estimated distance between the sensor unit and the occupant based on an integrated value of a phase change amount of the output of the sensor unit; and a bio-signal output determination unit which determines reliability of the bio-signal based on the estimated distance and stops the output of the bio-signal in a case where the reliability is low.

The sensor unit includes a local oscillator, a transmission antenna, a receiving antenna, a distributor, or a mixer, and a transmission signal is radiated toward a driver. A local signal $T(t)$ having a frequency fHz expressed by, for example, $T(t)=\cos(2\pi ft)$ is emitted from the local oscillator, and a part of the emitted electric wave is reflected and received by the receiving antenna as a receiving signal $R(t)$ approximated by $R(t)=\cos(2\pi ft-4\pi d(t)/\lambda-4\pi x(t)/\lambda)$ (wherein $d(x)$ is a distance displacement between the sensor unit and the driver, $x(t)$ is a fine distance displacement of a body surface including heart rate or respiration of the driver, and $\lambda$ is a wavelength of the local signal $T(t)$).

The receiving signal $R(t)$ is distributed into two by the distributor and input into two mixers. In addition, one more local signal $T(t)$ distributed by the distributor is distributed into two in a state where only one phase is shifted by $\pi/4$ radian by the distributor, and is input into each of two mixers, and the local signal $T(t)$ and the receiving signal $R(t)$ are mixed with each other. A base band component which is close to a DC region and a modulation component are output by a multiplication operation in the two mixers, but as each of the output signals passes through a low pass filter, a real part $Bi(t)$ and an imaginary part $Bq(t)$ which are expressed as follows in the base band receiving signal including only the base band component, are obtained.

$Bi(t)=\frac{1}{2} \cos(4\pi d(t)/\pi+4\pi x(t)/\lambda)$ $Bq(t)=\frac{1}{2} \cos(\pi/4+4\pi d(t)/\lambda+4\pi x(t)/\lambda)$ These parts are converted into a digital signal from an analog signal by an AD converter, and are input to a bio-signal extract unit as a detected signal output by the sensor unit.

In addition, JP-A-2011-015887 discloses a biological state obtaining apparatus or the like which can obtain a bio-signal of a living body in a non-contact manner, and can obtain information related to a biological state without performing complicated processing, such as frequency analysis with respect to a bio-signal. The biological state obtaining apparatus includes: an IQ signal obtaining part which transmits an electromagnetic wave to a body surface of the living body, IQ-wave-detects a reflected wave thereof, and consecutively obtains an I signal and a Q signal which are output from an IQ-wave detector that outputs the I signal and the Q signal in a time series; and a biological state obtaining part which obtains a state of the living body based on a trajectory on an IQ plane of an obtained signal obtained by the IQ signal obtaining part.

SUMMARY

However, in the above-described related art, the distance, inclination, and reflectivity of the body surface of the living body change as the human body moves, and thus, the electric wave strength of the reflected wave changes. Therefore, it is difficult to accurately detect the fine movement of the body surface caused by the heart rate or respiration. In addition, in order to detect the fine movement of the body surface caused by the heart rate or respiration, even when using the signal obtained by AD-converting the I signal/Q signal, there is a problem that resolving power of the AD conversion is not sufficient.

One or more embodiments of the invention provide an electric wave type biosensor which accurately senses bio-information which is accompanied with the fine movement, such as heart rate, in the electric wave type biosensor that uses a Doppler sensor.

According to one or more embodiments of the invention, there is provided an electric wave type biosensor including: an electromagnetic wave irradiation unit which irradiates a body surface of a living body with an electromagnetic wave; a reflected wave receiving unit which receives a reflected wave obtained as the electromagnetic wave irradiated by the electromagnetic wave irradiation unit and then reflected on the body surface, and obtains an I signal obtained by multiplying the irradiated electromagnetic wave signal and the received reflected signal, and a Q signal obtained by delaying the I signal only by a predetermined phase; a differentiation calculation unit which differentiates the I signal and the Q signal which are obtained by the reflected wave receiving unit, and calculates an I signal differential value and the Q signal differential value; and an angular velocity calculation unit which calculates an angular velocity of the I signal and the Q signal, based on the I signal and a Q signal which are obtained by the reflected wave receiving unit and the I signal differential value and the Q signal differential value which are calculated by the differentiation calculation unit based on the I signal and the Q signal.

According to this, it is possible to provide an electric wave type biosensor which accurately senses the bio-information which is accompanied with the fine movement, such as the heart rate.

In the electric wave type biosensor, a bio-information extract unit which extracts bio-information of the living body based on the angular velocity calculated by the angular velocity calculation unit, may further be provided.

According to this, it is possible to detect various pieces of bio-information.

According to one or more embodiments of the invention, it is possible to provide an electric wave type biosensor which accurately senses bio-information which is accompanied with fine movement, such as heart rate, in the electric wave type biosensor that uses a Doppler sensor.

BRIEF DESCRIPTION OF THE DRAWINGS

FIG. 6 is a graph illustrating the bio-information extracted by the electric wave type biosensor of the embodiment of the invention;

DETAILED DESCRIPTION

In embodiments of the invention, numerous specific details are set forth in order to provide a thorough understanding of the invention. However, it will be apparent to one of ordinary skill in the art that the invention may be practiced without these specific details. In other instances, well-known features have not been described in detail to avoid obscuring the invention.

Hereinafter, an embodiment of the invention will be described with reference to the drawings. An electric wave type biosensor according to the embodiment of the invention irradiates a human body surface with an electromagnetic wave by using a Doppler sensor, obtains a differential value of an I signal and a Q signal of a reflected wave thereof, and accordingly, obtains the bio-information which is accompanied with fine movement included in the reflected wave.

An electric wave type biosensor 100 in the embodiment will be described with reference to FIGS. 1 to 4. The electric wave type biosensor 100 is installed in equipment having a surface which is directly or indirectly in contact with a part of the human body, and senses the bio-information of a user of the equipment. Here, the equipment (general term of tool, machinery, and machine) having a surface which is in contact with a part of the human body is specifically referred to as, for example, a chair or a sofa on which a human sits, a bed on which a human lies down, a body inspection equipment installed in a hospital, and a seat which is installed in a vehicle or an airplane and on which a human sits.

A surface which is in contact with a part of the human body is referred to as a seat surface or a backrest surface in a chair or the like, and a mattress upper surface in a bed. The surface may be directly or indirectly in contact with a part of the human body, or may indirectly come into contact with the human body as a human wears clothes. A part of the body is a buttock or a thigh on a seat surface of a chair or the like, and is generally referred to as the back in the backrest of a chair or the like or in a bed or the like. In the body inspection equipment, a part of the body may be any of arms and legs of a human.

In the specification, the bio-information of the user is referred to as the size of the heart rate (pulse rate) or a pulse wave, or respiratory frequency or the size of respiration, and does not include cough or sneeze which generates movement of skin or muscle which does not come from the heart rate or respiration. The heart rate or the respiration generates fine movement on the body surface of the living body, and the electric wave type biosensor 100 detects the bio-information that is accompanied with the fine movement.

Figure 1:
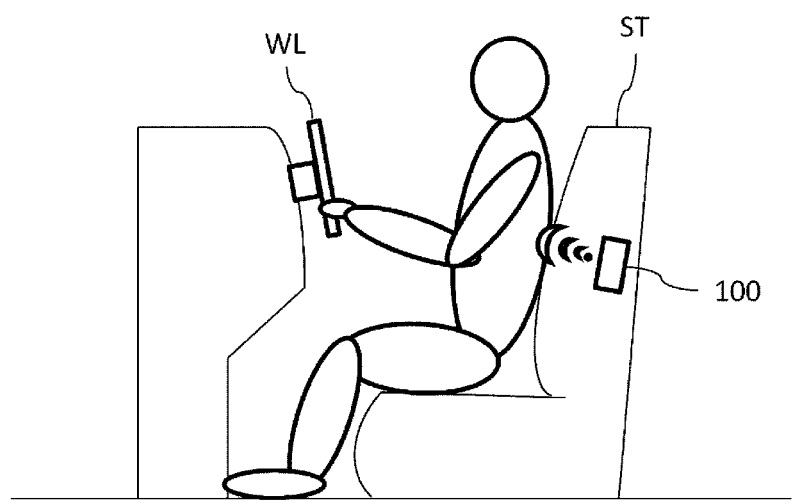
FIG. 1 is a schematic view in which an electric wave type biosensor according to a embodiment of the invention is installed in a vehicle interior of a vehicle.

In the embodiment, a case where the electric wave type biosensor 100 is installed in an interior of a vehicle as illustrated in FIG. 1 will be described. The electric wave type biosensor 100 is installed in a backrest portion of a seat ST on which the driver or the like sits. Since the purpose of the electric wave type biosensor 100 is to sense the fine movement of the skin surface which is accompanied with the heart rate or respiration, a case where the electric wave type biosensor 100 is installed in the backrest portion which is a surface that is in contact with the back of the driver who does not have a relatively large movement is more preferable than a case where the electric wave type biosensor 100 senses the movement by irradiating a face or the like of the driver who has a large movement in a forward handle WL direction with an electric wave.

Figure 2:
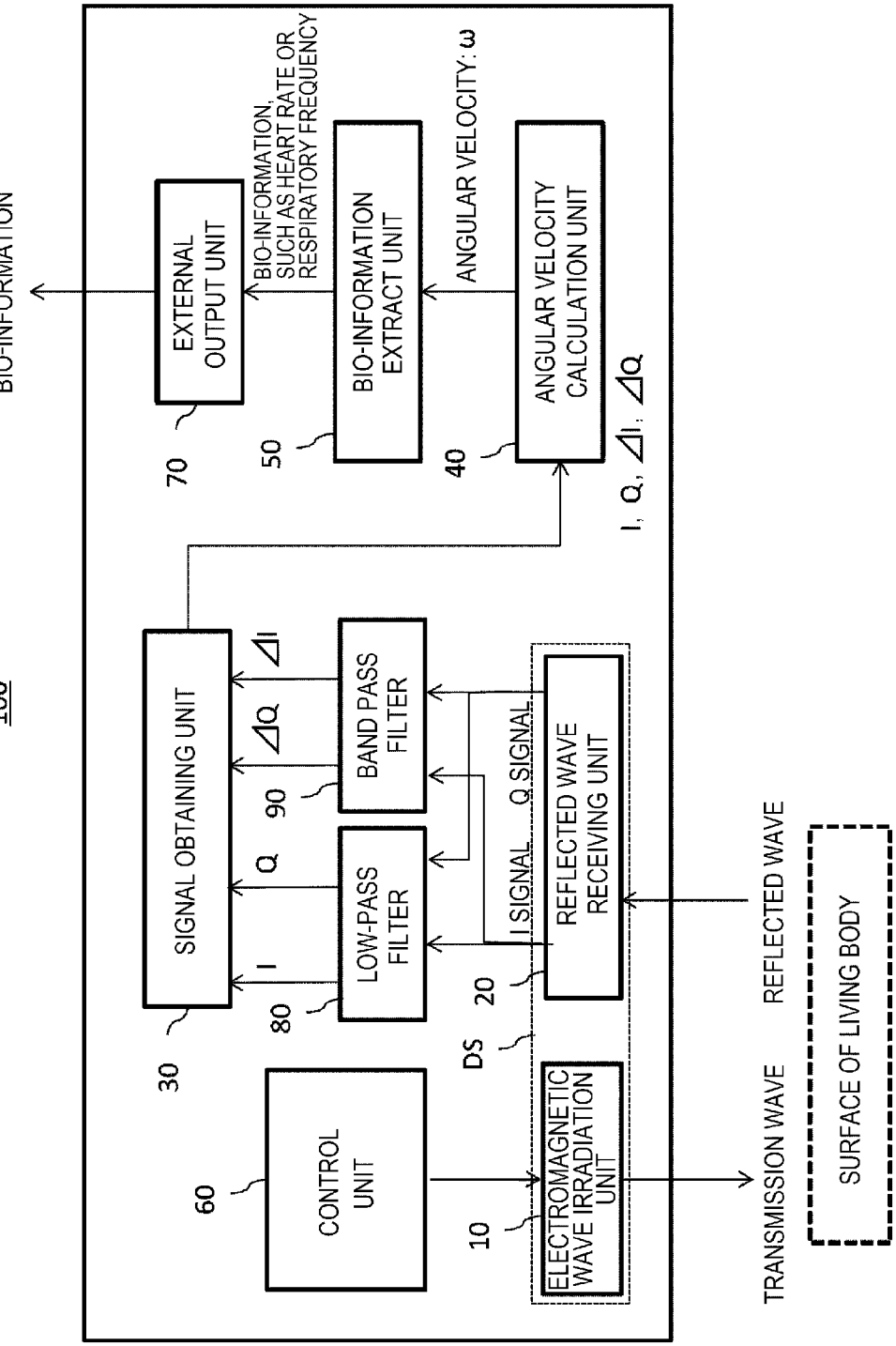
FIG. 2 is a block diagram of the electric wave type biosensor of the embodiment of the invention.

As illustrated in FIG. 2, the electric wave type biosensor 100 includes an electromagnetic wave irradiation unit 10 which irradiates the body surface of the living body with the electromagnetic wave; a reflected wave receiving unit 20 which obtains an I signal obtained by multiplying the signal of the irradiated electromagnetic wave and the received reflected signal, and a Q signal obtained by delaying the I signal by a predetermined phase, after the reflected wave obtained as the electromagnetic wave irradiated by the electromagnetic wave irradiation unit 10 is reflected on the body surface is received and wave detection or amplification is performed; and a control unit 60 which controls the electromagnetic wave irradiation unit 10. In addition, the electromagnetic wave irradiation unit 10 and the reflected wave receiving unit 20 configure a Doppler sensor DS.

Figure 3:
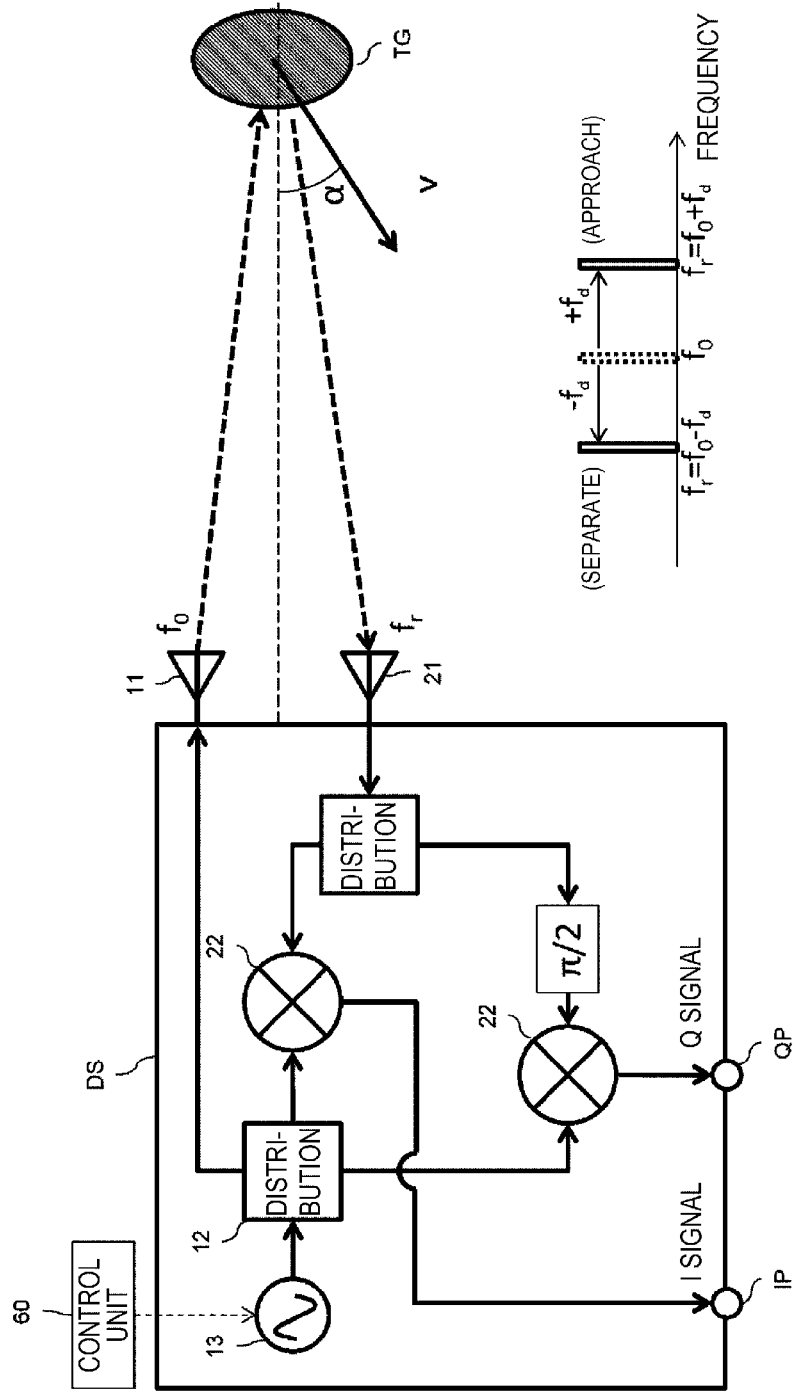
FIG. 3 is a block diagram of a Doppler sensor in the electric wave type biosensor of the embodiment of the invention.

FIG. 3 is a block diagram specifically illustrating the Doppler sensor DS. An oscillator 13 of the Doppler sensor DS oscillates at a predetermined frequency by a control of the control unit 60. In addition, a microwave band of the frequency is generally used, and there are many cases where the frequency is not particularly limited, but 24 GHz is generally used in a case of a use for obtaining the bio-information. The electromagnetic wave oscillated by the oscillator 13 is distributed by a distributor 12, and a measurement target TG is irradiated with one of the electromagnetic waves as an electromagnetic wave having a frequency $f_0$ (for example, 24 GHz) from a transmission antenna 11.

The electromagnetic wave of the frequency $f_0$ is reflected abutting against the measurement target TG having a movement, the frequency changes to frequency $f_r$, and a receiving antenna 21 receives the reflected wave that becomes the frequency $f_r$. In addition, the measurement target TG moves at a relative velocity v in a direction having an intersecting angle α with respect to directions of the transmission antenna 11 and the receiving antenna 21. Then, reflected wave frequency $f_r$ is acquired by the equation (1).

$$f_r = f_0 \pm f_d \quad (1)$$

A transmission wave frequency is $f_0$, a Doppler frequency is $f_d = (2f_0|v|/c_0) \cdot \cos \alpha$, a light velocity is $c_0$, a relative movement velocity of the measurement target is v, and an intersecting angle in the moving direction of the measurement target with respect to the transmission wave is α.

The reflected wave of the frequency $f_r$ received by the receiving antenna 21 is computed to be multiplied with the other electromagnetic wave (frequency $f_0$) distributed by the distributor 12 in a mixer 22, and is output from an I signal output port IP which is a part of the reflected wave receiving unit 20 as the I signal including a base band component that is close to a DC region and a modulation component. In addition, the reflected wave which is a reflected wave of the frequency $f_r$ received by the receiving antenna 21 and of which a phase is shifted by π/2, is similarly computed to be multiplied with the other electromagnetic wave (frequency $f_0$) distributed by the distributor 12 in the mixer 22, and is output from a Q signal output port QP which is a part of the reflected wave receiving unit 20 as the Q signal including the base band component that is close to the DC region and the modulation component.

The electric wave type biosensor 100 further includes a low pass filter 80 and a band pass filter 90 into which the I signal output from the I signal output port IP and the Q signal output from the Q signal output port QP by the reflected wave receiving unit 20 are input; and a signal obtaining unit 30 which obtains a signal which will be described later from each of the low pass filter 80 and the band pass filter 90. The low pass filter 80 is an arbitrary filter which removes noise of a high-frequency component and allows only the base band component to pass through in the I signal and the Q signal output by the I signal output port IP and the Q signal output port QP, and outputs signals (I and Q) that are the smoothed I signal and Q signal. In addition, since the purpose of the electric wave type biosensor 100 is to obtain the bio-information, such as heart rate or respiration, the low pass filter 80 is a filter which allows a heart rate of approximately 1 Hz or respiration of approximately 0.3 Hz to pass, and for example, is a filter which removes the heart rate or respiration which is equal to or greater than 10 Hz.

The band pass filter 90 is an embodiment of a differentiation calculation unit for obtaining differential values (ΔI and ΔQ) of each signal by removing a DC component from the I signal and the Q signal which are output by the I signal output port IP and the Q signal output port QP. In addition, the differential values (ΔI and ΔQ) obtained by the band pass filter 90 are linear approximate values, and the differentiation calculation unit is not limited to the band pass filter 90, and may be a unit which differentiates the I signal and the Q signal and calculates an I signal differential value ΔI and a Q signal differential value ΔQ.

Figure 4:
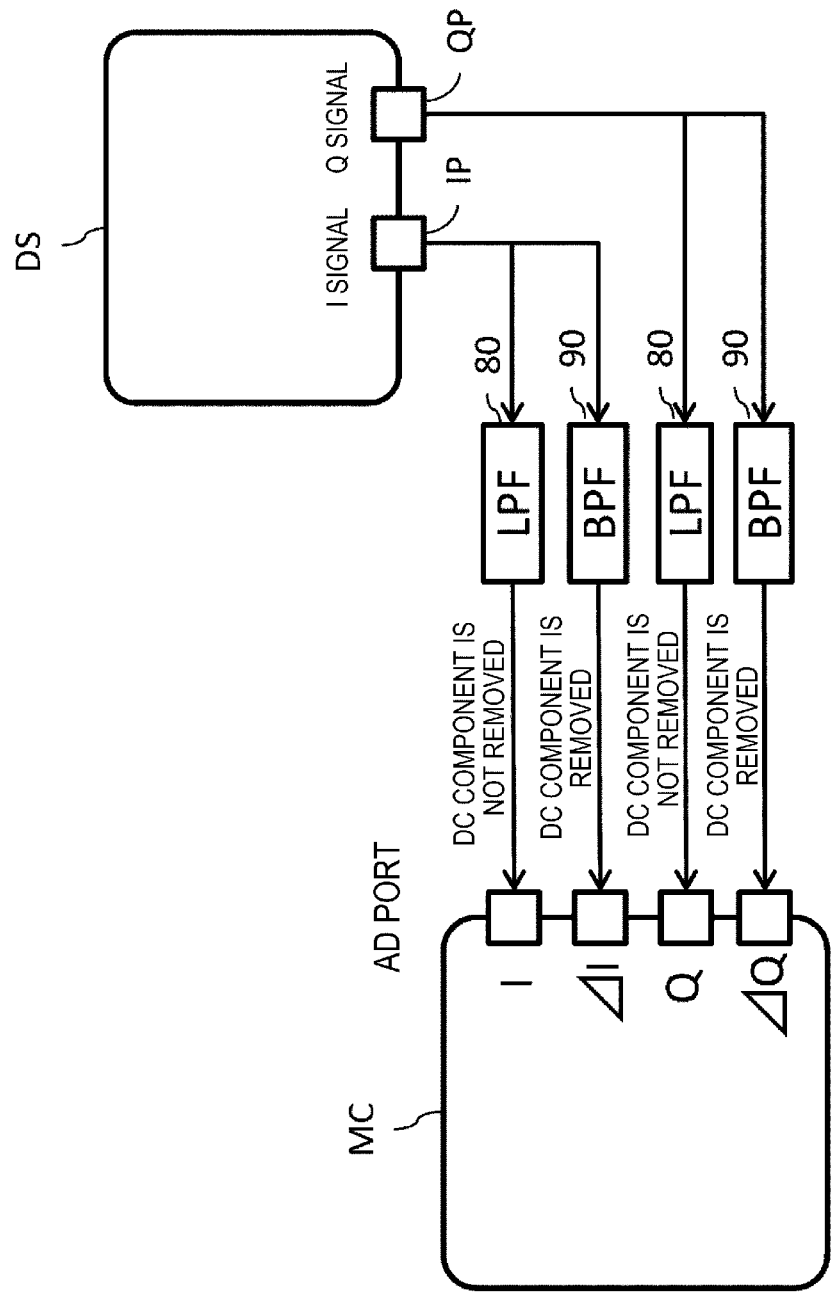
FIG. 4 is a schematic view illustrating a relationship of the Doppler sensor, a low pass filter and a band pass filter, and a microcomputer, in the electric wave type biosensor of the embodiment of the invention.

The signal obtaining unit 30 receives the I signal and the Q signal of which the high-frequency component is removed by the low pass filter 80, and the I signal differential value ΔI which is a differential value of the I signal from the band pass filter 90 and the Q signal differential value ΔQ which is a differential value of the Q signal. In addition, from the viewpoint of a physical configuration, as illustrated in FIG. 4, the I signal output from the I signal output port IP of the Doppler sensor DS is input into the low pass filter 80, and the I signal of which the high-frequency component is removed by the low pass filter 80 is input into an I port of an AD port of a microcomputer MC which is the signal obtaining unit 30. In addition, the I signal output from the I signal output port IP is input into the band pass filter 90, and the I signal of which the DC component is removed by the band pass filter 90 is input into a ΔI port of the AD port of the microcomputer MC which is the signal obtaining unit 30 as the I signal differential value ΔI.

In addition, the Q signal output from the Q signal output port QP of the Doppler sensor DS is input into the low pass filter 80, and Q signal of which the high-frequency component is removed by the low pass filter 80 is input into a Q port of the AD port of the microcomputer MC which is the signal obtaining unit 30. In addition, the Q signal output from the Q signal output port QP is input into the band pass filter 90, and the Q signal of which the DC component is removed by the band pass filter 90 is input into a ΔQ port of the AD port of the microcomputer MC which is the signal obtaining unit 30 as the Q signal differential value ΔQ. In addition, the microcomputer MC may include the above-described control unit 60, an angular velocity calculation unit 40 which will be described later, a bio-information extract unit 50, and an external output unit 70. In addition, each of the AD ports is connected to an AD converter, and is a port which converts an analog signal into a digital signal.

The electric wave type biosensor 100 further includes the angular velocity calculation unit 40 which calculates the angular velocity of the I signal and the Q signal, based on the I signal and the Q signal which are obtained by the reflected wave receiving unit 20 and the I signal differential value ΔI and the Q signal differential value ΔQ which are calculated by the differentiation calculation unit 90 based on the I signal and the Q signal. As will be described in the following, the angular velocity calculation unit 40 acquires an angular velocity ω of the I signal and the Q signal based on the I signal, the Q signal, the I signal differential value ΔI, and the Q signal differential value ΔQ.

A transmission wave $x_s(t)$ of the frequency $f_0$ in accordance with time t, which is transmitted by the transmission antenna 11 of the Doppler sensor DS, is expressed by the equation (2).

$$x_s(t) = A_s \cos(\omega_s t) \quad (2)$$

A transmission wave amplitude is $A_s$, and a transmission wave angular velocity is $\omega_s = 2\pi f_0$.

In addition, a reflected wave $x_r(t)$ of the frequency $f_r$ in accordance with time t, which is received by the receiving antenna 21 of the Doppler sensor DS, is expressed by the equation (3).

$$x_r(t) = A_r \cos([\omega_s \pm \omega_d]t + \phi) \quad (3)$$

A receiving wave amplitude is $A_r$, a Doppler angular velocity is $\omega_d = 2\pi f_d$, and a phase which depends on a distance to the measurement target is $\phi$.

In addition, a signal which is computed to be multiplied by inputting the transmission wave and the reflected wave into the mixer 22, is expressed by the equation (4).

$$x_s(t)x_r(t) = A_s A_r \cos(\omega_s t)\cos([\omega_s + \omega_d]t + \phi) = (A_s A_r/2)\{\cos(\omega_d t + \phi) + \cos([2\omega_s + \omega_d]t + \phi)\} \quad (4)$$

In a case where the high-frequency component is removed by the low pass filter 80, the modulation component of a second member in the equation (4) is removed. Then, I(t) which is the I signal after extracting the Doppler frequency component by the low pass filter 80 is expressed by the equation (5).

$$I(t) = (A_s A_r/2)\cos(\omega_d t + \phi) \quad (5)$$

In addition, Q(t) which is the Q signal obtained by delaying the phase by $\pi/2$ from the I signal is expressed by the equation (6).

$$Q(t) = (A_s A_r/2)\cos(\omega_d t + \phi - \pi/2) \quad (6)$$

The I signal represented by the equation (5) and the Q signal represented by the equation (6) are input into the signal obtaining unit 30.

In addition, since the I signal differential value $\Delta I$ is $\Delta I \approx dI/dt$, and the Q signal differential value $\Delta Q$ is $\Delta Q \approx dQ/dt$, when each of the equation (5) and the equation (6) is differentiated by the time t, the I signal differential value $\Delta I$ and the Q signal differential value $\Delta Q$ can be calculated.

Figure 7:
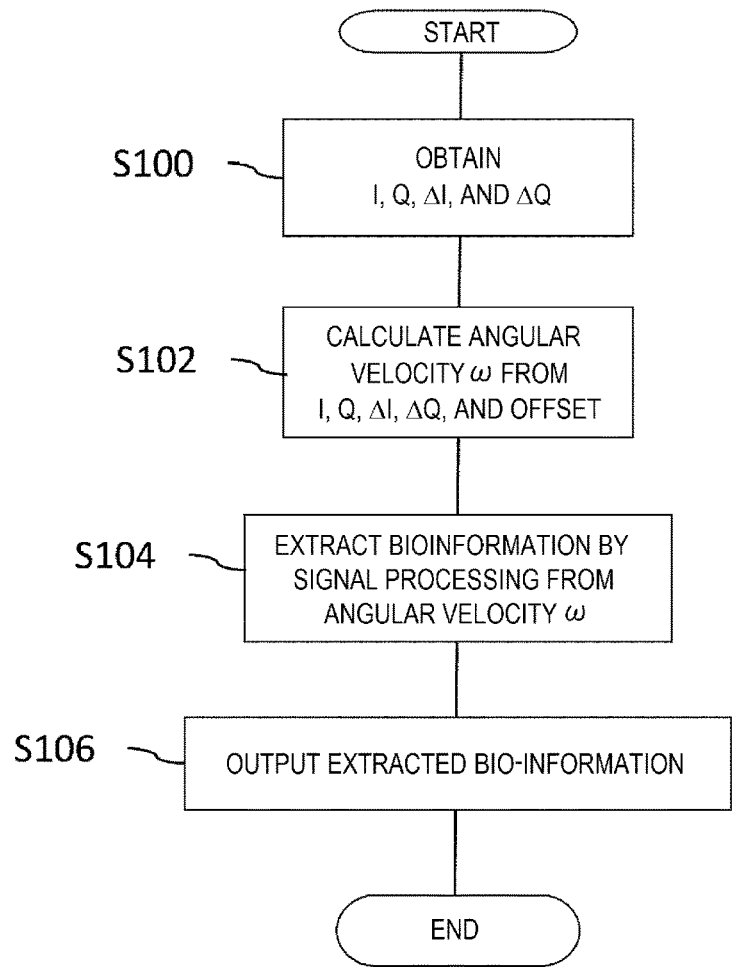
FIG. 7 is a flowchart illustrating a control in the electric wave type biosensor of the embodiment of the invention.

In addition, the angular velocity $\omega$ on the I-Q coordinate plane as illustrated in FIG. 7 is $\omega = d\theta/dt$.

In addition, since $\theta = \arctan(I - I_{offset})/(Q - Q_{offset})$ when $I_{offset}$ can be expressed by a constant defined by an installation condition of the electric wave type biosensor, and $Q_{offset}$ can be expressed by a constant defined by an installation condition of the electric wave type biosensor, the angular velocity $\omega$ can be expressed by Expression 1 as follows:

$$\omega \approx \frac{(I - I_{offset}) \times \Delta Q - (Q - Q_{offset}) \times \Delta I}{(I - I_{offset})^2 + (Q - Q_{offset})^2} \quad \text{(Expression 1)}$$

Figure 8:
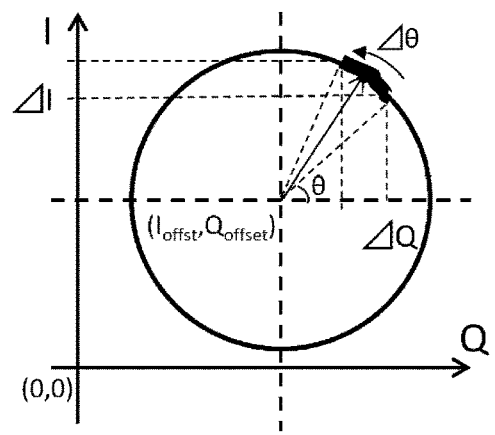
FIG. 8 is a view for describing the angular velocity or the like on an I-Q coordinate plane.

In addition, the size of a circle in FIG. 8 indicates the size of receiving strength in the receiving antenna 21 of the reflected wave, and fluctuates according to a state (distance, inclination of the reflected surface, reflectivity, or the like) of the surface of the living body which is the measurement target TG. In a case where the distance between the Doppler sensor DS and the surface of the living body is d, and a displacement amount $\Delta d$ of the distance d is expressed by the equation (7).

$$\Delta d = \lambda \cdot \Delta \theta / 4\pi \quad (7)$$

$\lambda$ is a wavelength (for example, 12.5 mm in a case where the frequency is 24 GHz) of the transmission wave.

For example, there is a case where the displacement amount $\Delta d$ increases when an upper half of the body of the driver largely moves, and the phase of $\theta$ becomes unclear. In addition, both of the movement of the surface of the living body generated by the heart rate or respiration and the movement of the surface of the living body generated by another large action of the human, are included in the movement of the surface of the living body, but it is difficult to detect the fine movement of the surface of the living body only by using the I signal/Q signal output by the Doppler sensor DS. For example, when the upper half of the body of the driver largely moves, the strength of the reflected wave largely fluctuates to be superior to the fine movement, such as the heart rate, and the fine movement of the surface of the living body cannot be detected.

Here, in the embodiment of the invention, since the movement of the surface of the living body caused by the large action of the human is substantially zero within an extremely short period of time, it is possible to extract the movement of the surface of the living body caused by the heart rate or respiration by considering the I signal differential value $\Delta I$ and the Q signal differential value $\Delta Q$. In addition, it is possible to accurately detect the bio-information which is accompanied with the fine movement on the body surface, such as heart rate or respiratory frequency, by calculating the angular velocity $\omega$ on an I signal and Q signal coordinate plane that is a change of a phase based on the above-described (Expression 1) not to be disturbed by the change in a state of the surface of the living body, such as the distance or the inclination of the reflected surface.

Figure 5A:
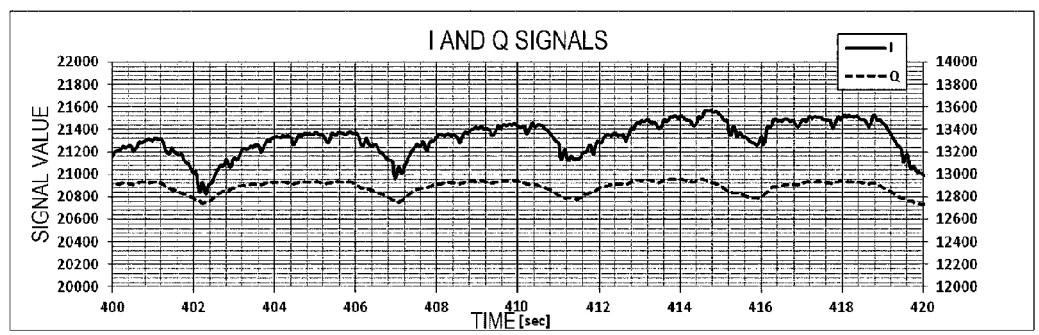
FIG. 5A is a graph illustrating an I signal and a Q signal which are obtained by a signal obtaining unit.
Figure 5B:
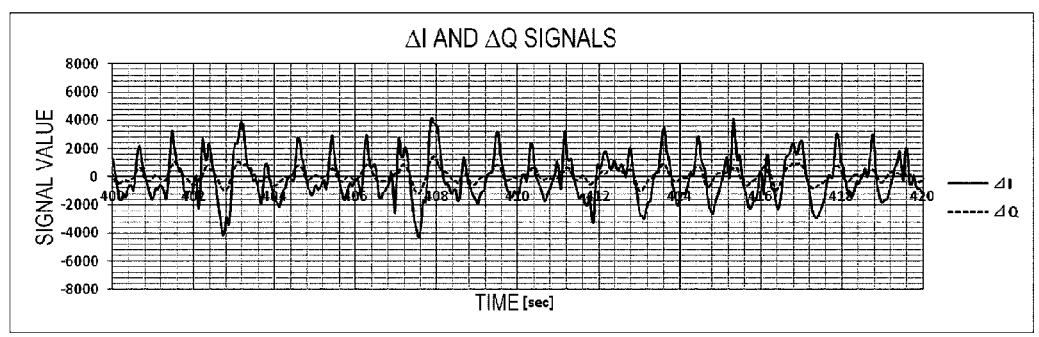
FIG. 5B is a graph illustrating an I signal differential value and a Q signal differential value which are obtained by the signal obtaining unit.

FIG. 5A is a graph illustrating the I signal and the Q signal which are obtained by the signal obtaining unit 30, and illustrates a time-series change of each signal of which the high-frequency component is removed while passing through the low pass filter 80 from the signal obtained from the surface of the living body. In addition, FIG. 5B is a graph illustrating the I signal differential value $\Delta I$ and the Q signal differential value $\Delta Q$ which are output by the band pass filter 90 (differentiation calculation unit), and illustrates the time-series change of each signal of which only the frequency of the heart rate component is allowed to pass through the band pass filter 90. In addition, the amplitude of the I signal differential value $\Delta I$ and the Q signal differential value $\Delta Q$ fluctuates according to the position of $\theta$, but the case of the drawing indicates a case where $\theta$ is positioned to be near an I axis on the I-Q coordinate plane in which the I signal differential value $\Delta I$ relatively largely fluctuates.

Figure 5C:
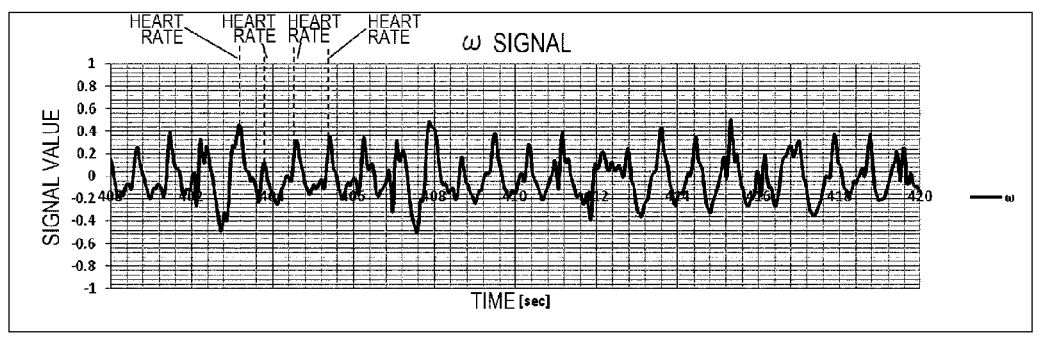
FIG. 5C is a graph illustrating an angular velocity which is related to a heart rate calculated by an angular velocity calculation unit, in the electric wave type biosensor of the embodiment of the invention.

In addition, FIG. 5C illustrates the time-series change of the angular velocity $\omega$ related to the heart rate calculated by the angular velocity calculation unit 40 in accordance with the (Expression 1), based on the I signal and the Q signal which are illustrated in FIG. 5A and the I signal differential value $\Delta I$ and the Q signal differential value $\Delta Q$ which are illustrated in FIG. 5B. As illustrated in FIG. 5C, only the heart rate is clearly illustrated by periodical peaks of the graph. In this manner, it is possible to provide the electric wave type biosensor 100 which accurately detects the fine movement by irradiating the surface of the human body with the electromagnetic wave, and by detecting the bio-information which is accompanied with the fine movement, such as the heart rate frequency or the respiratory frequency, based on the angular velocity on the coordinate plane of the I signal and the Q signal of the reflected wave.

In addition, as a modification of the embodiment, the electric wave type biosensor 100 can further include the bio-information extract unit 50 which extracts the bio-information of the living body based on the angular velocity $\omega$ calculated by the angular velocity calculation unit 40. The bio-information extract unit 50 extracts the bio-information based on the characteristics of the bio-information to be extracted. For example, FIG. 6 is a graph of the bio-information illustrated by the angular velocity ω output by the angular velocity calculation unit 40. In the case of FIG. 6, the frequency component which passed through the band pass filter 90 in the previous stage is also allowed to pass not only the frequency of the heart rate component but also the frequency component of respiration. In the case, the angular velocity ω output by the angular velocity calculation unit 40 is obtained by synthesizing two of the periodical component of respiration and the periodical component of heart rate.

In this manner, in a case where the angular velocity ω obtained by synthesizing two of the periodical component of respiration and the periodical component of heart rate is input to the bio-information extract unit 50, the bio-information extract unit 50 can extract the heart rate or the respiratory frequency or the strengths from the heights of each of the peaks by comparing the period of general respiration or heart rate. In this manner, by irradiating the human body surface with the electromagnetic wave, by obtaining a plural pieces of bio-information based on the angular velocity on the coordinate plane of the I signal and the Q signal of the reflected wave, and by extracting a specific bio-information based on the frequency component, such as general heart rate or respiratory frequency, it is possible to obtain various pieces of bio-information at the same time.

In addition, the electric wave type biosensor 100 further includes the external output unit 70 for outputting the bio-information to the external mechanism which uses the bio-information illustrated by the angular velocity ω calculated by the angular velocity calculation unit 40 or the bio-information extracted by the bio-information extract unit 50.

FIG. 7 is a flowchart illustrating a control in the electric wave type biosensor 100. In addition, S in the flowchart indicates steps. In S100, each of the AD ports which is the signal obtaining unit 30 of the electric wave type biosensor 100 obtains the I signal and the Q signal which passed through the low pass filter 80 and the I signal differential value ΔI and the Q signal differential value ΔQ which passed through the band pass filter 90. In S102, the angular velocity calculation unit 40 calculates the angular velocity ω based on the above-described (Expression 1), from the I signal, the Q signal, the I signal differential value ΔI, and the Q signal differential value ΔQ, which are obtained by the signal obtaining unit 30, and the offset values defined by the installation condition of the electric wave type biosensor 100.

In S104, the bio-information extract unit 50 extracts the bio-information to be extracted from the angular velocity ω calculated by the angular velocity calculation unit 40 by signal processing. In addition, in S106, the external output unit 70 outputs the extracted bio-information to the external mechanism.

In addition, the invention is not limited to the exemplified embodiment, and can be realized according to a configuration within a range that does not depart from the contents described in each of the claims. In other words, the invention is illustrated in the drawings mainly particularly regarding the specific embodiment, and is described, but without departing from the technical idea and the range of object, those skilled in the art can add various deformations in the number of components and other specific configurations, with respect to the above-described embodiment.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. An electric wave type biosensor comprising:
an electromagnetic wave irradiation unit which irradiates a body surface of a living body with an electromagnetic wave;
a reflected wave receiving unit which receives a reflected wave obtained as the electromagnetic wave irradiated by the electromagnetic wave irradiation unit and then reflected on the body surface, and obtains an I signal obtained by multiplying the irradiated electromagnetic wave signal and the received reflected signal, and a Q signal obtained by delaying the I signal only by a predetermined phase;
a differentiation calculation unit which differentiates the I signal and the Q signal which are obtained by the reflected wave receiving unit, and calculates an I signal differential value and a Q signal differential value; and
an angular velocity calculation unit which calculates an angular velocity of the I signal and the Q signal, based on the I signal and the Q signal which are obtained by the reflected wave receiving unit and the I signal differential value and the Q signal differential value which are calculated by the differentiation calculation unit based on the I signal and the Q signal,
wherein the angular velocity is a function of a sum of a square of I−$I_{offset}$ and a square of Q−$Q_{offset}$, where I is the I signal, $I_{offest}$ is a first constant defined by an installation condition of the electric wave type biosensor, Q is the Q signal, and $Q_{offset}$ is a second constant defined by the installation condition of the electric wave type biosensor.

2. The electric wave type biosensor according to claim 1, further comprising:
a bio-information extract unit which extracts bio-information of the living body based on the angular velocity calculated by the angular velocity calculation unit.

3. The electric wave type biosensor according to claim 1, wherein
the angular velocity is calculated using the following equation $$\omega \approx \frac{(I - I_{offset}) \times \Delta Q - (Q - Q_{offset}) \times \Delta I}{(I - I_{offset})^2 + (Q - Q_{offset})^2},$$

and
ω is the angular velocity, ΔQ is the Q signal differential value, and ΔI is the I signal differential value.

* * * * *